(12) United States Patent
Fricker et al.

(10) Patent No.: US 7,294,771 B1
(45) Date of Patent: Nov. 13, 2007

(54) MATADOR GT TALL FESCUE

(75) Inventors: Crystal Fricker, Canby, OR (US);
Melodee L. Fraser, Zebulon, NC (US);
Joseph K. Wipff, Canby, OR (US)

(73) Assignee: Pure Seed Testing, Inc., Canby, OR (US)

( * ) Notice: Subject to any disclaimer, the term of this patent is extended or adjusted under 35 U.S.C. 154(b) by 338 days.

(21) Appl. No.: 10/927,420

(22) Filed: Aug. 25, 2004

(51) Int. Cl.
*A01H 5/00* (2006.01)
*A01H 5/10* (2006.01)
*A01H 1/00* (2006.01)

(52) U.S. Cl. ............... 800/320; 800/266; 800/278; 800/298; 800/300

(58) Field of Classification Search ........... 800/260, 800/265, 298, 300
See application file for complete search history.

(56) References Cited

U.S. PATENT DOCUMENTS 6,066,786 A    5/2000   Rose-Fricker 6,423,887 B1 *  7/2002   Rose-Fricker ............... 800/320

OTHER PUBLICATIONS

Poehlman, J.M. and D.A. Sleper. 1995. Breeding Field Crops. 4th ed. Iowa State University Press, Ames, Iowa, p. 473.*
Fraser et al. 2001. Crop Sci. 41: 1997-1998.*
Turf-Seed, Inc., Pure Seed Testing, Inc., *Field Day 22*, Jun. 17, 2004, Front cover and pp. 16-18 and 43-68.
Turf-Seed, Inc. Pricing Guideline Fall 2004, Aug. 1, 2004.

* cited by examiner

*Primary Examiner*—David H. Kruse
*Assistant Examiner*—Keith O. Robinson
(74) *Attorney, Agent, or Firm*—Klarquist Sparkman, LLP

(57) ABSTRACT

A glyphosate-tolerant tall fescue (*Festuca arundinacea*) variety in one form known as Matador GT (experimental code PST-5TU0), seed used to produce the grass, and methods of using the grass plant and the seed are provided. This grass is suitable for use in lawns, athletic fields, golf courses, sod, and other turfs where weeds are a problem. Weed control in areas planted with the disclosed grasses can be achieved by direct application of glyphosate herbicides, for example at a rate of at least 4 ounces per acre, such as at least 8 ounces per acre.

31 Claims, No Drawings

MATADOR GT TALL FESCUE

FIELD

This disclosure relates to a tall fescue grass that is tolerant to glyphosate at levels sufficient to remove grass weed species from various turfs. One particular example of this grass is known as Matador GT (experimental code PST-5TU0).

BACKGROUND

Fescue grasses (*Festuca* species) are widely used as turf in a variety of applications, including home lawns, golf courses, athletic fields, parks, pasture and along roadsides. Two types of fescue grasses are most commonly grown: tall fescues and fine fescues. Tall fescue grasses (such as *F. arundinacea*) have excellent drought and wear resistance. Tall fescue is adapted to a wide range of climactic conditions and is the most predominant cool-season, perennial grass in the United States. (See *Tall Fescue*, Edited by Buckner and Bush, Published by the American Society of Agronomy, Crop Science Society of America, and Soil Science Society of America. ASA Monograph Number 20. 1979. ISBN 0-89118-057-5). The term fine fescue encompasses several sub-types including hard fescue grasses (*F. longifolia*); these grasses are low maintenance and shade tolerant, but lack the durability of tall fescue grasses.

Glyphosate (N-(phosphonomethyl) glycine) is the active ingredient in glyphosate herbicides, such as ROUNDUP® herbicide produced by Monsanto, St. Louis, Mo., Credit® herbicide produced by Nufarm, Inc. (Australia), and Razor® herbicide produced by Nufarm Turf and Specialty (Burr Ridge, Ill.). Typically, glyphosate is formulated as a water-soluble salt such as an ammonium, alkylamine, alkali metal or trimethylsulfonium salt. One of the most common formulations is the isopropylamine salt of glyphosate, which is the form employed in ROUNDUP® herbicide.

Glyphosate is a broad spectrum herbicide that inhibits the enzyme enolpyruvylshikimate-phosphate synthase (ESPS). It is conventionally applied as an aqueous solution to the foliage of plants, where it is taken up into the leaves and transported throughout the plant. Commercial formulations of glyphosate may also include one or more surfactants to facilitate penetration of the active ingredient into the plant leaves, as well as compounds to enhance rainfastness. Numerous U.S. patents disclose various formulations of glyphosate, including U.S. Pat. Nos. 4,405,531; 5,118,338; 5,196,044; 5,639,711; 5,652,197; 5,679,621; and 5,750,468.

Therefore, it is desirable to identify plants, such as grass turfs, that are naturally tolerant to glyphosate herbicides. Such tolerant plants can be planted in areas treated with glyphosate herbicides.

SUMMARY OF THE DISCLOSURE

Herein disclosed is a tall fescue which is sufficiently glyphosate tolerant to survive applications of glyphosate herbicides at levels sufficient to kill many common grass weeds that grow in fescue plantings, and which has moderate brown patch resistance. One example of such a glyphosate tolerate tall fescue is termed Matador GT (Matador glyphosate tolerant; experimental code PST-5TU0). As used herein, a glyphosate-tolerant fescue grass is capable of tolerating application of herbicide effective applications, such as at least about 4 ounces per acre, such as at least about 8 ounces per acre, of agricultural grade formulations of glyphosate-based herbicides (such as ROUNDUP®, Credit®, and Razor® brand herbicides (equivalent to application of approximately 0.014 g/square meter and 0.028 g/square meter of the active ingredient, glyphosate, respectively).

In one example, Matador GT is tolerant to application of least ¼ pint per acre of agricultural grade formulations of glyphosate-based herbicides (equivalent to application of approximately 0.014 g/square meter of glyphosate). In another example, Matador GT is tolerant to application of least ½ pint per acre of agricultural grade formulations of glyphosate-based herbicides (equivalent to application of approximately 0.028 g/square meter of glyphosate). Use of this grass as turf (for example in lawns, in turf, in sod, on golf courses (such as on a golf tee, fairway or rough), in parks, in athletic fields, and along roadsides) permits ready control of weeds by application of a glyphosate herbicide. In addition, the Matador GT variety has been observed under growing conditions in Hubbard, Oreg. (in 2002) to have an average mature plant height of about 80 cm, an average internode length of about 15 cm, an average flag leaf height of about 40 cm, an average tiller leaf length of 15 cm and an average tiller leaf width of 7 mm, an average flag leaf length of 11 cm and an average flag leaf width of 5.6 mm, an average panicle length of about 18 cm, an average lemma length of 5.7 mm, and an average awn length of 1.1 mm. In some examples, Matador GT has one or more of the following characteristics: a semierect growth habitat, no rhizomes, semi-rough leaf blade margins which are dark green in color, a panicle (at seed maturity) that is narrow-tapering with a pubescent branch.

At least 2500 seeds of the Matador GT variety have been deposited with the American Type Culture Collection (ATCC, Manassas, Va.; ATCC Deposit No. PTA-5790). Therefore, these seeds are known and readily available to the public.

In one example, the disclosure provides tall fescue plants that include the morphological and physiological characteristics of Matador GT, as well as seeds of such plants. In some examples, the disclosure provides tall fescue plants having the genotype of Matador GT. The disclosure also encompasses tall fescue plants that are produced by crossing Matador GT with other grass varieties, as well as seeds of such plants.

Methods of producing grass seed are also provided. The method includes growing Matador GT grass plants and setting progeny seed, and then harvesting the progeny seed. In some examples the method also includes planting seed from Matador GT under conditions that result in the germination of the seed.

The present disclosure also provides methods of producing a glyphosate-tolerant grass plant by crossing a Matador GT variety (or a glyphosate-tolerant cross derived from Matador GT) with one or more other grass plants to produce progeny grass plants, and then screening the progeny grass plants to select a progeny grass plant that is tolerant to glyphosate. Screening can include contacting the progeny grass plants with at least ¼ pint per acre of glyphosate, such as at least ½ pint per acre, and selecting grass plants that survive the glyphosate treatment. Glyphosate-tolerant grass plants produced by this method are also encompassed by the disclosure.

These and other aspects of the present disclosure will become more apparent from the following description.

DETAILED DESCRIPTION OF SEVERAL EMBODIMENTS

The following examples are provided to better describe the present disclosure and to guide those of ordinary skill in the art in the practice of the present disclosure. As used herein and in the appended claims, the singular forms "a" or "an" or "the" include plural references unless the context clearly dictates otherwise. For example, reference to "a transgene" includes a plurality of such transgenes and reference to "the seed" includes reference to one or more seeds and equivalents thereof known to those skilled in the art, and so forth. Similarly, the word "or" is intended to include "and" unless the context clearly indicates otherwise. Hence "comprising A or B" means including A, or B, or A and B.

Unless explained otherwise, all technical and scientific terms used herein have the same meaning as commonly understood to one of ordinary skill in the art to which this disclosure belongs.

EXAMPLE 1

Origin and Breeding History of Tall Fescue Variety Matador GT (PST-5TU0)

The Matador GT tall fescue (*Festuca arundinacea*) variety was developed by Pure Seed Testing, Inc. as part of a breeding program to develop cultivars with herbicide tolerance. The plants that produced the breeder seed of Matador GT traced their maternal origins to plants that were selected for genetic tolerance to one or more of the following herbicides: diclofop, glufosinate, glyphosate and imazethapyr. These plants were selected through herbicide screening projects conducted by Pure Seed Testing, Inc. near Hubbard, Oreg. The plants used in this project were screened by applying a selective pressure method which allowed for the selection of surviving plants treated with herbicides at various stages of growth, as disclosed herein.

The initial tall fescue herbicide screening trials that led to the development of Matador GT were conducted in 1993, when populations of 'Apache II', 'Tomahawk', 'Coronado', PST-5S9 and PST-5ST were sprayed with various rates of diclofop and populations of Apache II, PST-5S9, Coronado, Tomahawk and PST-5PM were sprayed with various rates of glyphosate. Plants that survived exposure to diclofop were selected and interpollinated during the summer of 1994 in a population designated PST-5HOE. Glyphosate survivors interpollinated during the summer of 1994 in a population designated PST-5U4.

During the fall of 1995, 18 plants from population PST-5HOE, two plants selected from population PST-5U4 and one plant of unknown origin were each vegetatively divided into 16 propagules that were used to establish an isolated spaced-plant clonal-row nursery near Hubbard. These plants interpollinated during the summer of 1996 and 1997 and seed was subsequently harvested and designated PST-5HU.

The fall of 1997 a nursery of 3100 plants was started from open pollinated seed of PST-5HU. This nursery was sprayed with 8 oz glyphosate in April 1998.

During the spring of 1999, 53 plants with dark green color, low growth habit, fine leaf texture and freedom from stem rust were selected from spaced-plant nurseries near Hubbard. Plants were selected from these nurseries which included a population of plants that were selected for brown patch resistance near Rolesville, N.C.; a nursery of PST-5HU; a nursery of 'Matador' and a population of PST-5ASR, which was developed into 'Silverstar'. The 53 selected plants were transplanted, prior to anthesis, into an isolated crossing block designated PST-5TU. During the summer of 1999, seed was harvested from 33 plants with good stem rust resistance and high floret fertility.

Seed from this harvest was used to establish an isolated 3300-plant nursery near Hubbard. During the spring of 2000, different herbicides were sprayed individually across different sections of the rows in this nursery. Glyphosate, imazethapyr and glufosinate were applied in February and glyphosate was applied in April. Prior to anthesis, 147 attractive surviving plants were selected and transplanted into an isolated crossing block designated PST-5TU0. These plants were allowed to interpollinate and seed was subsequently harvested during the summer of 2000.

During the late summer of 2000, 103 plants that had shown high seed yield and good stem rust resistance in the PST-5TU0 crossing block were each vegetatively divided into 25 propagules. In addition, 47 plants from population PST-5BU were each divided into 10 propagules each. PST-5BU was a population of plants that had been selected for brown patch resistance and glyphosate tolerance. These plants from PST-5TU0 and PST-5BU were transplanted into an isolated clonal-row nursery near Hubbard during the fall of 2000. Each of these rows was sprayed with 16 oz/acre glyphosate in April 2001.

Fifty-two PST-5TU0 clones were identified as exhibiting glyphosate tolerance, stem rust resistance and high floret fertility. Seed was harvested from the plants in each of these clonal rows and bulked by row during the summer of 2001. The seed from 19 clones that had exhibited superior turf quality in progeny trials in Oregon and North Carolina were bulked together to produce Breeder seed of Matador RT. These 19 clones traced their maternal origins to the following sources: 42% to Matador; 21% to 'OnCue'; 15% to Apache II; 6% to a population designated "Hoelon comp", which traced its origin to Tomahawk, Apache II and Coronado; 5% to Silverstar; 5% to PST-5S9, which traced its origin to Tomahawk, 'Safari', 'Silverado' and 'Rebel Jr.'; 3% to Coronado and 3% to PST-5 ST, which traced its origin to Tomahawk and 'Virtue'.

An additional 33 PST-5TU0 clones were harvested but not used in the breeder seed, which provided additional pollen in this nursery, traced their maternal origins to these sources: 15 to Matador; nine to PST-5HU; five to OnCue; one to Coronado; one to Silverstar and one to Tomahawk. Seven teen clones from the 5BU population also provided pollen in this nursery. These clones traced their maternal origins to the following sources: five to Coronado; three to Silverado; three to a plant collected in Holly Springs, Miss.; two to 'Tar Heel'; two to population PST-R5MR; one to 'Apache' and one to population PST-511.

Seed production of Matador GT is limited to three generations of increase from Breeder seed: one each of Foundation, Registered and Certified. Pure Seed Testing, Inc. maintains Breeder seed in Oregon. Matador GT is a stable and uniform cultivar. Fewer than 2% off-types or variants have been observed in the production or multiplication of Matador GT tall fescue.

fall of 2001. Tillers from 25 plants in each of four replications were measured in 2002 and 2003 in the spaced-plant trials in each of the three replications in the seed yield trail. Variations on these measurements may be observed for plants of differing ages, grown in other locations and/or under different prevailing weather conditions.

Matador GT is most similar to Matador tall fescue. However, these two varieties differ in at least the following characteristics: Matador GT has a mean internode length at least 1 cm longer than Matador (Tables 1-3); Matador GT has a mean flag leaf height at least 2.8 cm taller than Matador (Tables 1-3); and Matador GT has a mean initial heading date at least 3 days earlier than Matador (Tables 4, 5).

TABLE 1

2002 mean morphological measurements for spaced-plant trial.

| Variety | Plant Height (cm) | Flag Leaf Height (cm) | Internode Length (cm) | Tiller Leaf Length (cm) | Tiller Leaf Width (mm) | Flag Leaf Length (cm) | Flag Leaf Width (mm) | Panicle Length (cm) | Tiller Count (#/100 cm$^2$) |
|---|---|---|---|---|---|---|---|---|---|
| Kentucky 31 | 130.5 | 71.3 | 27.4 | 23.9 | 8.5 | 17.2 | 6.6 | 27.6 | 38.3 |
| Rebel Jr. | 85.3 | 41.1 | 14.3 | 18.7 | 8.8 | 14.7 | 7.5 | 22.2 | 39.1 |
| Matador GT | 80.3 | 39.5 | 14.9 | 14.8 | 7.1 | 11.2 | 5.6 | 18.3 | 50.3 |
| Matador | 79.6 | 36.1 | 13.3 | 13.6 | 6.2 | 10.9 | 5.3 | 16.0 | 55.9 |
| LSD (0.05)* | 3.6 | 2.4 | 1.1 | 1.1 | 0.5 | 1.0 | 0.6 | 1.1 | 12.1 |

*To determine statistical differences among entries, subtract one entry's mean from another entry's mean. Statistical differences occur when this value is equal to or larger than the corresponding L.S.D. value.

TABLE 2

2003 mean morphological measurements for spaced-plant trial.

| Variety | Plant Height (cm) | Flag Leaf Height (cm) | Internode Length (cm) | Tiller Leaf Length (cm) | Tiller Leaf Width (mm) | Flag Leaf Length (cm) | Flag Leaf Width (mm) | Panicle Length (cm) | Tiller Count (#/100 cm$^2$) |
|---|---|---|---|---|---|---|---|---|---|
| Kentucky 31 | 145.2 | 96.4 | 31.4 | 37.3 | 9.4 | 23.8 | 8.1 | 35.7 | 352.1 |
| Rebel Jr. | 116.2 | 68.8 | 23.4 | 26.7 | 5.6 | 20.7 | 4.9 | 27.3 | 278.6 |
| Matador GT | 109.2 | 65.9 | 24.3 | 21.7 | 4.7 | 17.3 | 3.8 | 21.6 | 384.1 |
| Matador | 107.9 | 59.6 | 23.2 | 22.7 | 4.4 | 16.7 | 4.0 | 20.6 | 400.4 |
| LSD (0.05)* | 6.2 | 5.5 | 1.4 | 1.6 | 0.4 | 1.4 | 0.4 | 2.7 | 81.1 |

*To determine statistical differences among entries, subtract one entry's mean from another entry's mean. Statistical differences occur when this value is equal to or larger than the corresponding L.S.D. value.

EXAMPLE 2

Seed Deposits

Seeds of the tall fescue variety Matador GT (experimental code PST-5TU0) were deposited with the ATCC (Manassas, Va.) on Jan. 23, 2004 under accession number PTA-5790. The variety is also maintained at, and available from, Pure Seed Testing, Inc., P.O. Box 449, Hubbard, Oreg. 97032.

EXAMPLE 3

Description of Plants

The following growth and morphological characteristics were observed for Matador GT plants that were approximately one or two years old, grown near Hubbard, Oreg. Tall fescue spaced-plant and seed yield trials were planted in the

TABLE 3

2002 mean morphological measurements for seed yield trial.

| Variety | Flag Leaf Height (cm) | Internode Length (cm) |
|---|---|---|
| Kentucky 31 | 96.7 | 30.7 |
| Matador GT | 72.4 | 29.1 |
| Matador | 69.6 | 26.0 |
| LSD (0.05)* | 3.7 | 1.8 |

*To determine statistical differences among entries, subtract one entry's mean from another entry's mean. Statistical differences occur when this value is equal to or larger than the corresponding L.S.D. value.

TABLE 4

2003 mean initial heading dates for seed yield trial seeded fall of 2002.

| Variety | Mean |
|---|---|
| Matador | 08 May |
| Matador GT | 05 May |
| Kentucky 31 | 15 Apr. |
| LSD (0.05)* | 3 days |

*To determine statistical differences among entries, subtract one entry's mean from another entry's mean. Statistical differences occur when this value is equal to or larger than the corresponding L.S.D. value.

TABLE 5

Mean initial heading dates for a single row yield trial seeded fall of 2001.

| Variety | 2002 | 2003 |
|---|---|---|
| Magellan | 12 May | 05 May |
| Matador | 12 May | 03 May |
| Matador GT | 30 Apr. | 29 Apr. |
| Kentucky 31 | 25 Apr. | 08 Apr. |
| LSD (0.05)* | *5 days | 8 days |

*To determine statistical differences among entries, subtract one entry's mean from another entry's mean. Statistical differences occur when this value is equal to or larger than the corresponding L.S.D. value.

EXAMPLE 4

Disease Resistance and Environmental Stress Tolerance

The following turf quality ratings were observed for Matador GT plants that were approximately one or two years old, grown in various regions of the United States. Tall fescue trials were seeded in the fall of 2000 or 2001. Variations on these measurements may be observed for plants of differing ages, grown in other locations and/or under different prevailing weather conditions. The data presented in Table 6 is expressed in numbers ranging from 1-9, with 1 representing low disease resistance or susceptible to environmental stress and 9 representing no disease and resistant to environmental stress.

TABLE 6

Disease and Stress tolerance of Matador GT

| Disease or Stress | Rating |
|---|---|
| Net blotch (*D. dictyoides*) | 7 |
| Brown patch (*Rhizoctonia solani*) | 5 |
| Stem Rust (*Puccinia graminis*) | 6 |
| *Pythium* blight (*Pythium* spp.) | 6 |
| Crown rust (*Puccinia coronata*) | 6 |
| Drought stress | 7 |
| Shade stress | 6 |
| Winter stress | 6 |

EXAMPLE 5

Turf Quality Characteristics

The following turf quality ratings were observed for Matador GT plants that were approximately one or two years old, grown in various regions of the United States (see Tables for particular locations). Tall fescue trials were seeded in the fall of 2000 or 2001. Variations on these measurements may be observed for plants of differing ages, grown in other locations and/or under different prevailing weather conditions.

The turf quality ratings presented in Tables 7-14 are expressed in numbers ranging from 1-9, with 1 representing low turf quality and 9 representing desirable high turf quality. The establishment ratings presented in Table 8 is expressed in numbers ranging from 1-9, with 1 representing 0% established and 9 representing 100% established. The color ratings presented in Table 11 are expressed in numbers ranging from 1-9, with 1 representing light green and 9 representing dark green color. The *Pythium* blight and brown patch ratings presented in Tables 12 and 14, and the cool-season *Rhizoctonia* ratings presented in Table 13, are expressed in numbers ranging from 1-9, with 1 representing disease and 9 representing no disease.

TABLE 7

Mean turf quality ratings for tall fescue turf trial seeded fall of 2000 near Camarillo, CA

| Entry | 2001 | 2002 | Mean |
|---|---|---|---|
| 85% Matador, 15% North Star | 8.1 | 7.8 | 8.0 |
| PST-DDL | 7.7 | 8.2 | 7.9 |
| Silverstar | 7.8 | 6.9 | 7.3 |
| Matador | 7.6 | 6.9 | 7.2 |
| Dynamic | 7.1 | 7.2 | 7.1 |
| PST-5BZ | 6.8 | 7.3 | 7.1 |
| PST-5DH | 7.2 | 6.7 | 6.9 |
| PST-5NAS | 6.9 | 6.9 | 6.9 |
| PST-5BEH | 6.6 | 7.2 | 6.9 |
| PST-5MP | 6.9 | 6.8 | 6.9 |
| PST-5LMD | 7.2 | 6.5 | 6.9 |
| Matador GT | 7.0 | 6.6 | 6.8 |
| Insignia | 6.6 | 7.0 | 6.8 |
| Millennium | 6.7 | 6.8 | 6.8 |
| PST-5BE | 6.9 | 6.6 | 6.7 |
| FL 100 | 6.3 | 7.1 | 6.7 |
| Success | 6.6 | 6.6 | 6.6 |
| Pure Gold | 6.7 | 6.4 | 6.5 |
| PST-5H2 | 6.3 | 6.8 | 6.5 |
| PST-5KI | 6.7 | 6.3 | 6.5 |
| PST-5DWF | 7.0 | 6.0 | 6.5 |
| Coronado | 6.6 | 6.3 | 6.4 |
| PST-5S2 | 6.1 | 6.8 | 6.4 |
| Silverado II | 6.1 | 6.7 | 6.4 |
| Durana | 6.6 | 6.0 | 6.3 |
| PST-5BAB | 6.2 | 6.3 | 6.3 |
| PST-5T2 | 6.7 | 5.4 | 6.0 |
| PST-5BR0 | 6.3 | 5.8 | 6.0 |
| OnCue | 6.1 | 5.8 | 5.9 |
| PST-R5AM | 5.8 | 6.0 | 5.9 |
| PST-R5MM | 5.8 | 5.8 | 5.8 |
| PST-523M | 6.0 | 5.5 | 5.8 |
| Dynasty | 5.8 | 5.6 | 5.7 |
| PST-5UP | 5.9 | 5.4 | 5.7 |
| Wolfpack | 5.7 | 5.6 | 5.6 |
| Olympic Gold | 5.7 | 5.5 | 5.6 |
| PST-5FH | 5.6 | 5.6 | 5.6 |
| Tar Heel | 6.0 | 5.1 | 5.5 |
| Coronado Gold | 5.9 | 5.2 | 5.5 |
| Tomahawk E | 5.8 | 5.3 | 5.5 |
| Bonsai 2000 | 5.3 | 5.7 | 5.5 |
| PST-R5EL | 5.3 | 5.6 | 5.5 |
| Endure | 5.6 | 5.3 | 5.4 |
| Endeavor | 5.4 | 5.2 | 5.3 |
| Apache II | 5.2 | 5.2 | 5.2 |
| Marksman | 5.1 | 4.7 | 4.9 |
| Silverado | 4.6 | 4.5 | 4.5 |
| Safari | 4.6 | 3.9 | 4.2 |
| Torpedo | 2.2 | 2.0 | 2.1 |
| LSD (0.05)* | 0.5 | 0.8 | 0.5 |

*To determine statistical differences among entries, subtract one entry's mean from another entry's mean. Statistical differences occur when this value is equal to or larger than the corresponding L.S.D. value.

TABLE 8

2002 mean establishment and turf quality ratings for turf trial seeded fall 2001 near Camarillo, CA

| Entry | Establishment (9 Jan.) | Turf Quality |
|---|---|---|
| PST-DDL | 6.3 | 7.4 |
| Matador | 6.3 | 7.3 |
| Matador GT | 6.0 | 7.2 |
| PST-53T | 5.7 | 7.2 |
| PST-5L0 | 6.7 | 6.9 |
| PST-5JM | 6.7 | 6.8 |
| PST-5BZ | 6.7 | 6.8 |
| Dynamic | 6.7 | 6.8 |
| PST-5NAS | 7.3 | 6.7 |
| Fidelity | 6.7 | 6.6 |
| Dynasty | 6.0 | 6.6 |
| Pure Gold | 6.3 | 6.4 |
| PST-5BAB | 7.3 | 6.4 |
| PST-5KI | 6.7 | 6.3 |
| Millennium | 6.7 | 6.3 |
| Apache III | 6.7 | 6.2 |
| Silverstar | 6.7 | 6.0 |
| Silverado II | 7.3 | 6.0 |
| Tar Heel II | 7.0 | 5.8 |
| Olympic Gold | 7.0 | 5.3 |
| Tomahawk | 7.0 | 5.3 |
| Tar Heel | 6.3 | 4.9 |
| Apache II | 6.7 | 4.9 |
| LSD (0.05)* | 1.1 | 0.6 |

*To determine statistical differences among entries, subtract one entry's mean from another entry's mean. Statistical differences occur when this value is equal to or larger than the corresponding L.S.D. value.

TABLE 9

Mean turf quality ratings for tall fescue turf trial seeded fall of 2000 near Hubbard, OR

| Variety | 2001 | 2002 | 2003 | Mean |
|---|---|---|---|---|
| Silverstar | 6.5 | 6.1 | 5.6 | 6.1 |
| PST-5NAS | 6.3 | 5.9 | 5.7 | 6.0 |
| Dynamic | 6.1 | 5.6 | 6.1 | 5.9 |
| SYN-5A3 | 6.0 | 5.7 | 5.9 | 5.9 |
| PST-5KI | 6.1 | 5.7 | 5.9 | 5.9 |
| Silverado II | 6.3 | 5.5 | 5.7 | 5.8 |
| Matador GT | 6.2 | 5.3 | 5.5 | 5.7 |
| Matador | 6.0 | 5.7 | 5.5 | 5.7 |
| PST-5H2 | 5.8 | 5.4 | 5.8 | 5.7 |
| SYN-5MP | 5.9 | 5.9 | 5.3 | 5.7 |
| PST-DDL | 5.9 | 5.6 | 5.4 | 5.6 |
| Gazelle | 5.9 | 5.6 | 5.4 | 5.6 |
| Olympic Gold | 5.6 | 5.7 | 5.6 | 5.6 |
| PST-R5AM | 5.5 | 5.7 | 5.6 | 5.6 |
| PST-5BAB | 6.1 | 5.5 | 5.3 | 5.6 |
| SYN-5BEH | 5.6 | 5.6 | 5.6 | 5.6 |
| SYN-5HU0 | 5.9 | 5.5 | 5.3 | 5.6 |
| SYN-5T2 | 5.8 | 5.4 | 5.8 | 5.6 |
| SYN-R5JM | 5.9 | 5.3 | 5.5 | 5.6 |
| PST-5BE | 5.8 | 5.4 | 5.4 | 5.5 |
| PST-5DH | 5.5 | 5.4 | 5.5 | 5.5 |
| Jaguar 3 | 5.3 | 5.6 | 5.5 | 5.5 |
| PST-5BR0 | 5.2 | 5.3 | 5.9 | 5.5 |
| PST-5BZ | 5.6 | 5.4 | 5.4 | 5.5 |
| PST-5DWF | 5.2 | 5.7 | 5.5 | 5.5 |
| SYN-5S2 | 5.5 | 5.4 | 5.7 | 5.5 |
| SYN-R54M | 5.7 | 5.4 | 5.3 | 5.5 |
| Endure | 5.6 | 5.1 | 5.4 | 5.4 |
| Pure Gold | 5.7 | 5.4 | 5.1 | 5.4 |
| PST-5LMD | 5.3 | 5.4 | 5.1 | 5.3 |
| Apache II | 5.8 | 5.0 | 5.0 | 5.3 |
| Coronado | 5.7 | 5.2 | 4.9 | 5.3 |
| Coronado Gold | 5.8 | 5.0 | 5.0 | 5.3 |
| Dominion | 5.2 | 5.4 | 5.1 | 5.3 |
| PST-R5MM | 5.4 | 5.5 | 5.2 | 5.3 |
| SYN-5BRE | 5.4 | 5.3 | 5.1 | 5.3 |

TABLE 9-continued

Mean turf quality ratings for tall fescue turf trial seeded fall of 2000 near Hubbard, OR

| Variety | 2001 | 2002 | 2003 | Mean |
|---|---|---|---|---|
| Tomahawk E | 5.4 | 5.1 | 5.3 | 5.3 |
| PST-5FH | 5.6 | 5.2 | 4.8 | 5.2 |
| PST-5UP | 5.2 | 5.1 | 5.4 | 5.2 |
| Bonanza II | 5.7 | 4.8 | 5.2 | 5.2 |
| Confederate | 5.2 | 5.6 | 4.8 | 5.2 |
| OnCue | 5.3 | 5.1 | 5.3 | 5.2 |
| Silverado | 4.9 | 5.5 | 5.3 | 5.2 |
| Summer Lawn | 5.5 | 5.3 | 4.8 | 5.2 |
| SYN-5G9 | 5.7 | 4.9 | 5.0 | 5.2 |
| Tar Heel | 5.1 | 5.3 | 5.3 | 5.2 |
| Wolfpack | 5.2 | 5.2 | 5.1 | 5.2 |
| PST-5PHR | 5.6 | 4.8 | 4.8 | 5.1 |
| Endeavor | 5.2 | 5.1 | 5.2 | 5.1 |
| PST-523M | 5.5 | 4.9 | 4.9 | 5.1 |
| Shortstop II | 5.5 | 5.1 | 4.7 | 5.1 |
| Tomahawk GT | 5.4 | 5.0 | 4.8 | 5.1 |
| PST-5NRR | 5.1 | 5.3 | 4.7 | 5.0 |
| Bandana | 4.9 | 4.9 | 5.1 | 5.0 |
| Bonsai | 5.3 | 5.0 | 4.8 | 5.0 |
| Virtue | 5.1 | 5.1 | 4.8 | 5.0 |
| Crossfire II | 4.8 | 5.0 | 4.9 | 4.9 |
| Grande | 5.0 | 4.7 | 4.8 | 4.9 |
| PST-RSEL | 5.2 | 5.0 | 4.6 | 4.9 |
| SYN-5CH | 5.2 | 4.7 | 4.8 | 4.9 |
| Trailblazer II | 4.8 | 4.7 | 4.9 | 4.8 |
| Adventure II | 4.6 | 5.0 | 4.7 | 4.7 |
| Avanti | 4.7 | 4.6 | 4.8 | 4.7 |
| Safari | 4.7 | 4.7 | 4.8 | 4.7 |
| Chapel Hill | 4.6 | 4.6 | 4.5 | 4.6 |
| Eldorado | 4.7 | 4.4 | 4.6 | 4.6 |
| Mustang II | 4.5 | 4.4 | 4.8 | 4.6 |
| Murietta | 4.2 | 4.2 | 4.3 | 4.2 |
| Torpedo | 3.5 | 3.3 | 4.3 | 3.4 |
| Kentucky 31 | 3.2 | 3.0 | 3.0 | 3.1 |
| LSD (0.05)* | 0.6 | 0.5 | 0.6 | 0.4 |

*To determine statistical differences among entries, subtract one entry's mean from another entry's mean. Statistical differences occur when this value is equal to or larger than the corresponding L.S.D. value.

TABLE 10

Mean turf quality ratings for tall fescue turf trial seeded fall 2001 near Hubbard, OR

| Variety | 2002 | 2003 | Mean |
|---|---|---|---|
| Padre | 6.0 | 5.7 | 5.8 |
| PST-DDL | 5.8 | 5.8 | 5.8 |
| PST-5BUL | 5.2 | 6.2 | 5.7 |
| BAR Fa 1005 | 5.5 | 5.7 | 5.6 |
| CAS-MC1 | 5.5 | 5.7 | 5.6 |
| L1F COMP | 5.7 | 5.4 | 5.6 |
| Matador GT | 5.8 | 5.4 | 5.6 |
| PST-5KB | 5.4 | 5.5 | 5.5 |
| CAS-ED | 5.5 | 5.5 | 5.5 |
| Guardian-21 | 5.3 | 5.7 | 5.5 |
| PST-5DH | 5.5 | 5.3 | 5.4 |
| Apache III | 5.1 | 5.6 | 5.4 |
| Focus | 5.4 | 5.5 | 5.4 |
| Matador | 5.2 | 5.6 | 5.4 |
| Magellan | 5.4 | 5.5 | 5.4 |
| Picasso | 5.1 | 5.7 | 5.4 |
| PST-53T | 5.5 | 5.3 | 5.4 |
| PST-5D01 | 5.5 | 5.3 | 5.4 |
| PST-5JM | 5.5 | 5.3 | 5.4 |
| PST-5PL | 5.3 | 5.5 | 5.4 |
| PST-5RZS | 5.6 | 5.2 | 5.4 |
| PST-5S12 | 5.5 | 5.4 | 5.4 |
| PST-5TDH | 5.2 | 5.5 | 5.4 |
| PST-5V1 | 5.4 | 5.4 | 5.4 |
| Silverado II | 5.3 | 5.6 | 5.4 |

TABLE 10-continued

Mean turf quality ratings for tall fescue turf trial seeded fall 2001 near Hubbard, OR

| Variety | 2002 | 2003 | Mean |
|---|---|---|---|
| SRX 8601 | 5.3 | 5.5 | 5.4 |
| SRX 8BE4 | 5.6 | 5.2 | 5.4 |
| Coronado | 5.3 | 5.3 | 5.3 |
| Durana | 5.3 | 5.2 | 5.3 |
| PST-5BUD | 5.3 | 5.3 | 5.3 |
| SR 8600 | 5.3 | 5.3 | 5.3 |
| Tahoe | 5.6 | 4.7 | 5.2 |
| Dynamic | 5.2 | 5.3 | 5.2 |
| Dynasty | 5.3 | 5.1 | 5.2 |
| Fidelity | 5.3 | 5.0 | 5.2 |
| Masterpiece | 5.1 | 5.3 | 5.2 |
| Millennium | 5.2 | 5.3 | 5.2 |
| MRF 210 | 5.4 | 5.1 | 5.2 |
| MRF 29 | 5.3 | 5.2 | 5.2 |
| Pick ZMG | 5.2 | 5.2 | 5.2 |
| PST-503 | 5.1 | 5.3 | 5.2 |
| PST-5BR0 | 5.1 | 5.4 | 5.2 |
| PST-5BU | 5.1 | 5.3 | 5.2 |
| PST-5BZ | 5.2 | 5.3 | 5.2 |
| PST-5PAL | 5.1 | 5.3 | 5.2 |
| PST-R5AM | 4.9 | 5.4 | 5.2 |
| SR 8250 | 5.1 | 5.3 | 5.2 |
| Tar Heel II | 5.3 | 5.2 | 5.2 |
| BAR Fa 1003 | 5.0 | 5.3 | 5.1 |
| Barrera | 5.3 | 5.0 | 5.1 |
| Biltmore | 4.7 | 5.5 | 5.1 |
| Dominion | 4.9 | 5.2 | 5.1 |
| MRF 25 | 5.4 | 4.9 | 5.1 |
| Pick 5M4 | 5.2 | 5.0 | 5.1 |
| Pick MT3 | 5.3 | 4.9 | 5.1 |
| Plantation | 5.1 | 5.2 | 5.1 |
| PST-5BAB | 5.0 | 5.1 | 5.1 |
| Silverstar | 5.2 | 5.0 | 5.1 |
| SRX 8FFT | 4.9 | 5.3 | 5.1 |
| Sunpro | 5.1 | 5.1 | 5.1 |
| TF 66 | 5.1 | 5.1 | 5.1 |
| Tomahawk E | 5.1 | 5.1 | 5.1 |
| PST-5LMD | 5.1 | 4.8 | 5.0 |
| Apache II | 5.0 | 5.0 | 5.0 |
| Barrington | 5.3 | 4.7 | 5.0 |
| Bingo | 5.2 | 4.8 | 5.0 |
| Laramie | 5.1 | 4.8 | 5.0 |
| NA-TDD | 4.8 | 5.3 | 5.0 |
| PST-5KI | 5.1 | 4.9 | 5.0 |
| PST-5PHR | 5.0 | 5.1 | 5.0 |
| Pure Gold | 5.0 | 5.0 | 5.0 |
| Rebel Sentry | 5.2 | 4.9 | 5.0 |
| Rembrandt | 5.0 | 5.0 | 5.0 |
| PST-5H2 | 4.8 | 5.0 | 4.9 |
| BAR Fa 1CR7 | 5.1 | 4.8 | 4.9 |
| Barlexas | 4.5 | 5.2 | 4.9 |
| Duster | 5.1 | 4.8 | 4.9 |
| Jaguar 3 | 4.7 | 5.0 | 4.9 |
| MRF 26 | 5.3 | 4.5 | 4.9 |
| Olympic Gold | 5.0 | 4.8 | 4.9 |
| PST-5G9 | 4.7 | 5.1 | 4.9 |
| PST-5NAS | 4.9 | 4.9 | 4.9 |
| PST-R5MM | 4.8 | 4.9 | 4.9 |
| T991 | 4.7 | 5.2 | 4.9 |
| Tracer | 5.2 | 4.7 | 4.9 |
| Wolfpack | 4.9 | 4.9 | 4.9 |
| Barlexas II | 4.8 | 4.8 | 4.8 |
| Coronado Gold | 4.8 | 4.8 | 4.8 |
| Endeavor | 4.7 | 5.0 | 4.8 |
| MRF 22 | 4.6 | 5.0 | 4.8 |
| MRF 27 | 5.0 | 4.7 | 4.8 |
| MRF 28 | 5.2 | 4.5 | 4.8 |
| PST-5E2 | 5.1 | 4.6 | 4.8 |
| PST-5FZD | 4.9 | 4.8 | 4.8 |
| PST-5L0 | 4.9 | 4.8 | 4.8 |
| PST-5TKR | 5.0 | 4.6 | 4.8 |
| Summer Lawn | 4.6 | 5.0 | 4.8 |
| Crewcut II | 4.6 | 4.8 | 4.7 |
| Endure | 4.6 | 4.8 | 4.7 |
| South Paw | 4.7 | 4.8 | 4.7 |
| Pick 00-AFA | 4.8 | 4.6 | 4.7 |
| PST-R5EL | 4.5 | 4.9 | 4.7 |
| Silverado | 4.3 | 5.2 | 4.7 |
| Tar Heel | 4.7 | 4.8 | 4.7 |
| Tomahawk GT | 4.8 | 4.7 | 4.7 |
| Confederate | 4.7 | 4.5 | 4.6 |
| Lancer E | 4.3 | 4.8 | 4.6 |
| Daytona | 4.6 | 4.6 | 4.6 |
| Bonsai | 4.0 | 4.9 | 4.5 |
| Falcon II | 4.2 | 4.8 | 4.5 |
| Southern Choice II | 4.4 | 4.6 | 4.5 |
| Bravo | 4.4 | 4.4 | 4.4 |
| Safari | 4.2 | 4.7 | 4.4 |
| Grande | 4.4 | 4.3 | 4.3 |
| Eldorado | 4.0 | 4.5 | 4.2 |
| Watchdog | 3.4 | 4.5 | 3.9 |
| Kentucky 31 E+ | 3.1 | 3.3 | 3.2 |
| LSD (0.05)* | 0.5 | 0.7 | 0.5 |

*To determine statistical differences among entries, subtract one entry's mean from another entry's mean. Statistical differences occur when this value is equal to or larger than the corresponding L.S.D. value.

TABLE 11

2003 mean color and turf quality ratings for tall fescue turf trial seeded fall of 2001 at Summit Seed, Manteno, IL

| Variety | Color* | Turf Quality |
|---|---|---|
| PST-5KI | 6.0 | 6.1 |
| Dynamic | 5.8 | 6.0 |
| Fidelity | 5.9 | 6.0 |
| Matador GT | 6.0 | 6.0 |
| PST-5JM | 6.1 | 6.0 |
| PST-5L0 | 5.8 | 6.0 |
| Silverado II | 5.8 | 6.0 |
| Silverstar | 5.9 | 6.0 |
| Tar Heel II | 5.9 | 6.0 |
| Tomahawk | 5.6 | 6.0 |
| PST-5BZ | 5.9 | 5.9 |
| PST-5NAS | 6.0 | 5.9 |
| Apache III | 5.9 | 5.9 |
| PST-DDL | 5.9 | 5.9 |
| Matador | 6.0 | 5.9 |
| PST-53T | 6.1 | 5.9 |
| PST-5BAB | 6.0 | 5.9 |
| Wolfpack | 5.5 | 5.9 |
| LSD (0.05) | 0.2 | 0.2 |

*To determine statistical differences among entries, subtract one entry's mean from another entry's mean. Statistical differences occur when this value is equal to or larger than the corresponding L.S.D. value.

TABLE 12

Mean turf quality, Pythium blight, and brown patch ratings for tall fescue turf trial seeded fall of 2001 near Rolesville, NC

| | Turf Quality | | | Pythium | Brown Patch | | |
|---|---|---|---|---|---|---|---|
| Variety | 2002 | 2003 | Mean | 21 Aug. 2003 | 2002 | 2003 | Mean |
| Tar Heel | 5.1 | 5.7 | 5.4 | 4.3 | 6.6 | 7.4 | 7.0 |
| Endeavor | 4.9 | 4.5 | 4.7 | 4.7 | 6.0 | 6.6 | 6.4 |
| Syn 5BUD | 5.1 | 6.2 | 5.6 | 2.7 | 5.6 | 7.2 | 6.4 |
| PST-5BR0 | 5.3 | 6.5 | 5.9 | 3.0 | 5.7 | 7.0 | 6.3 |
| PST-5V1 | 5.6 | 6.0 | 5.8 | 4.7 | 6.0 | 6.6 | 6.3 |
| PST-5K1 | 5.2 | 5.1 | 5.2 | 3.0 | 5.2 | 7.2 | 6.2 |
| PST-R5MM | 5.4 | 6.0 | 5.7 | 5.0 | 5.8 | 6.4 | 6.1 |

TABLE 12-continued

Mean turf quality, Pythium blight, and brown patch ratings for tall fescue turf trial seeded fall of 2001 near Rolesville, NC

| Variety | Turf Quality 2002 | 2003 | Mean | Pythium 21 Aug. 2003 | Brown Patch 2002 | 2003 | Mean |
|---|---|---|---|---|---|---|---|
| Silverado II | 4.9 | 5.9 | 5.4 | 4.7 | 6.1 | 6.0 | 6.1 |
| PST-5BAB | 5.7 | 5.7 | 5.7 | 3.7 | 5.2 | 6.8 | 6.0 |
| PST-5L0 | 4.9 | 6.0 | 5.4 | 5.7 | 4.7 | 7.3 | 6.0 |
| Fidelity | 5.1 | 5.9 | 5.5 | 3.7 | 5.9 | 6.1 | 6.0 |
| Summer Lawn | 4.9 | 4.3 | 4.6 | 4.3 | 5.6 | 6.4 | 6.0 |
| Tar Heel II | 6.1 | 6.5 | 6.3 | 5.3 | 6.8 | 5.1 | 5.9 |
| Wolfpack | 5.3 | 5.1 | 5.2 | 5.7 | 5.4 | 6.4 | 5.9 |
| 10762 | 5.3 | 6.5 | 5.9 | 3.3 | 5.0 | 6.3 | 5.6 |
| 10768 | 4.7 | 5.2 | 4.9 | 6.0 | 4.4 | 6.8 | 5.6 |
| Magellan | 4.7 | 5.8 | 5.3 | 4.0 | 4.9 | 6.3 | 5.6 |
| PST-5TKR | 4.9 | 5.4 | 5.2 | 4.0 | 5.3 | 5.9 | 5.6 |
| Silverstar | 5.4 | 5.5 | 5.5 | 3.0 | 5.0 | 6.3 | 5.6 |
| Syn 503 | 4.6 | 5.1 | 4.9 | 5.0 | 4.4 | 6.8 | 5.6 |
| Syn 5TDH | 4.7 | 5.9 | 5.3 | 2.3 | 5.0 | 5.9 | 5.5 |
| PST-5NAS | 5.4 | 5.3 | 5.3 | 4.0 | 3.9 | 6.8 | 5.4 |
| Syn 5BU | 4.7 | 5.1 | 4.9 | 4.3 | 5.8 | 5.1 | 5.4 |
| Syn 5G9 | 4.8 | 4.8 | 4.8 | 5.3 | 5.2 | 5.6 | 5.4 |
| Syn 5PAL | 4.9 | 4.9 | 4.9 | 3.0 | 6.0 | 4.8 | 5.4 |
| 10767 | 4.6 | 5.8 | 5.2 | 3.3 | 4.7 | 5.8 | 5.3 |
| 10771 | 3.6 | 4.5 | 4.0 | 4.3 | 4.1 | 6.5 | 5.3 |
| PST-5H2 | 5.5 | 5.8 | 5.7 | 4.7 | 5.2 | 5.4 | 5.3 |
| PST-5FZD | 4.9 | 6.2 | 5.6 | 2.3 | 4.2 | 6.3 | 5.3 |
| PST-5JM | 4.9 | 5.5 | 5.2 | 4.0 | 4.2 | 6.4 | 5.3 |
| SR 8550 | 4.5 | 4.5 | 4.5 | 5.7 | 4.0 | 6.7 | 5.3 |
| Olympic Gold | 5.3 | 5.6 | 5.5 | 2.7 | 4.6 | 5.9 | 5.2 |
| PST-5S12 | 4.9 | 5.3 | 5.1 | 5.3 | 4.0 | 6.4 | 5.2 |
| Padre | 5.8 | 6.2 | 6.0 | 4.7 | 4.6 | 5.7 | 5.1 |
| Syn 5DO1 | 4.5 | 5.3 | 4.9 | 3.7 | 4.4 | 5.7 | 5.1 |
| 10751 | 4.3 | 5.0 | 4.7 | 3.3 | 4.7 | 5.3 | 5.0 |
| 10754 | 4.2 | 4.5 | 4.3 | 3.3 | 4.3 | 5.7 | 5.0 |
| 10764 | 3.6 | 4.6 | 4.1 | 3.3 | 3.8 | 6.3 | 5.0 |
| Bingo | 5.1 | 5.4 | 5.2 | 4.7 | 4.2 | 5.8 | 5.0 |
| Matador GT | 5.5 | 5.7 | 5.6 | 4.7 | 4.1 | 5.9 | 5.0 |
| Guardian-21 | 5.6 | 5.9 | 5.7 | 4.7 | 4.4 | 5.5 | 5.0 |
| Syn 5E2 | 3.9 | 5.0 | 4.5 | 4.7 | 4.3 | 5.8 | 5.0 |
| 10761 | 4.3 | 4.3 | 4.3 | 4.7 | 4.6 | 5.2 | 4.9 |
| Jaguar 3 | 4.3 | 4.3 | 4.3 | 4.3 | 4.0 | 5.8 | 4.9 |
| SR 8250 | 5.3 | 4.6 | 5.0 | 3.3 | 3.6 | 6.3 | 4.9 |
| 10573 | 4.4 | 4.3 | 4.4 | 4.3 | 3.7 | 5.8 | 4.8 |
| BAR Fa 1005 | 4.7 | 5.5 | 5.1 | 3.3 | 4.0 | 5.7 | 4.8 |
| CAS-MCI | 4.4 | 4.9 | 4.7 | 4.0 | 3.0 | 6.5 | 4.8 |
| Confederate | 4.4 | 3.5 | 4.0 | 4.3 | 5.1 | 4.6 | 4.8 |
| Daytona | 4.2 | 4.5 | 4.3 | 3.7 | 3.8 | 5.8 | 4.8 |
| Picasso | 4.7 | 5.0 | 4.8 | 4.0 | 4.0 | 5.5 | 4.8 |
| SRX 8601 | 5.0 | 5.1 | 5.0 | 4.0 | 4.4 | 5.1 | 4.8 |
| 10757 | 3.8 | 4.4 | 4.1 | 5.0 | 4.3 | 5.0 | 4.7 |
| CAS-ED | 4.8 | 4.5 | 4.7 | 3.3 | 3.4 | 6.0 | 4.7 |
| Endure | 3.9 | 4.5 | 4.2 | 5.3 | 4.9 | 4.6 | 4.7 |
| L1F Comp | 5.1 | 4.9 | 5.0 | 3.3 | 3.2 | 6.2 | 4.7 |
| OnCue | 4.2 | 5.1 | 4.6 | 3.7 | 3.6 | 5.9 | 4.7 |
| Plantation | 5.0 | 5.2 | 5.1 | 5.0 | 4.9 | 4.4 | 4.7 |
| Tomahawk | 4.3 | 4.3 | 4.3 | 3.3 | 3.9 | 5.6 | 4.7 |
| Apache III | 5.0 | 5.3 | 5.1 | 4.7 | 4.8 | 4.3 | 4.6 |
| L11 Comp | 4.2 | 4.6 | 4.4 | 3.3 | 4.8 | 4.5 | 4.6 |
| Pick 00-AFA | 5.3 | 4.6 | 5.0 | 2.7 | 3.4 | 5.8 | 4.6 |
| Pick ZMG | 4.5 | 4.9 | 4.7 | 3.3 | 3.8 | 5.5 | 4.6 |
| MRF 27 | 3.4 | 4.0 | 3.7 | 4.3 | 2.8 | 6.2 | 4.5 |
| Pick 5M4 | 4.4 | 4.9 | 4.7 | 3.3 | 3.3 | 5.8 | 4.5 |
| PST-DDL | 3.9 | 4.3 | 4.1 | 3.3 | 2.9 | 6.1 | 4.5 |
| Rembrandt | 5.1 | 5.3 | 5.2 | 4.0 | 2.8 | 6.2 | 4.5 |
| Masterpiece | 5.1 | 5.4 | 5.2 | 3.0 | 3.8 | 5.1 | 4.4 |
| Pick MT3 | 5.1 | 5.6 | 5.3 | 3.7 | 3.8 | 5.1 | 4.4 |
| PST-R5AM | 4.7 | 5.1 | 4.9 | 4.3 | 3.8 | 5.1 | 4.4 |
| Rebel Sentry | 4.1 | 3.5 | 3.8 | 4.3 | 2.9 | 5.9 | 4.4 |
| SR 8600 | 5.2 | 5.3 | 5.3 | 2.3 | 4.7 | 4.2 | 4.4 |
| Syn 5BUL | 4.5 | 4.4 | 4.4 | 4.3 | 3.8 | 5.0 | 4.4 |
| 10763 | 3.6 | 4.0 | 3.8 | 3.0 | 3.6 | 5.1 | 4.3 |
| 10766 | 3.9 | 4.1 | 4.0 | 3.0 | 3.4 | 5.1 | 4.3 |
| Apache II | 4.6 | 4.5 | 4.6 | 2.7 | 4.1 | 4.6 | 4.3 |
| BAR Fa 1003 | 3.8 | 3.7 | 3.8 | 4.7 | 2.4 | 6.1 | 4.3 |
| Durana | 4.5 | 4.7 | 4.6 | 3.7 | 3.2 | 5.3 | 4.3 |
| MRF 210 | 4.4 | 4.8 | 4.6 | 2.3 | 3.2 | 5.3 | 4.3 |
| MRF 26 | 4.1 | 4.0 | 4.1 | 5.0 | 2.8 | 5.9 | 4.3 |
| Pure Gold | 3.6 | 3.7 | 3.6 | 4.3 | 3.0 | 5.7 | 4.3 |
| 10770 | 3.9 | 3.9 | 3.9 | 5.3 | 2.9 | 5.4 | 4.2 |
| PST-5RZS | 3.8 | 4.3 | 4.0 | 3.3 | 3.6 | 4.8 | 4.2 |
| Barlexas II | 5.8 | 5.4 | 5.6 | 3.3 | 4.3 | 4.1 | 4.2 |
| Dynasty | 5.2 | 5.2 | 5.2 | 2.7 | 3.4 | 5.0 | 4.2 |
| Safari | 3.9 | 3.0 | 3.4 | 5.0 | 3.1 | 5.3 | 4.2 |
| Silverado | 3.4 | 2.9 | 3.2 | 3.0 | 2.6 | 5.9 | 4.2 |
| SRX 8FFT | 4.9 | 4.6 | 4.7 | 4.3 | 4.0 | 4.4 | 4.2 |
| 10755 | 3.9 | 3.4 | 3.6 | 2.3 | 3.8 | 4.4 | 4.1 |
| 10759 | 3.7 | 4.0 | 3.9 | 4.3 | 3.7 | 4.5 | 4.1 |
| 10765 | 3.8 | 3.9 | 3.8 | 4.0 | 3.1 | 5.1 | 4.1 |
| Biltmore | 4.9 | 4.5 | 4.7 | 3.3 | 3.6 | 4.6 | 4.1 |
| Duster | 4.9 | 4.7 | 4.8 | 3.7 | 3.2 | 5.0 | 4.1 |
| Focus | 4.7 | 4.8 | 4.7 | 3.3 | 3.6 | 4.6 | 4.1 |
| Matador | 4.4 | 3.5 | 4.0 | 3.7 | 4.1 | 4.0 | 4.1 |
| South Paw | 3.8 | 3.6 | 3.7 | 2.7 | 3.3 | 4.8 | 4.1 |
| MRF 28 | 3.7 | 4.4 | 4.0 | 3.3 | 3.4 | 4.8 | 4.1 |
| NA-TDD | 4.8 | 5.3 | 5.0 | 3.3 | 3.7 | 4.5 | 4.1 |
| PST-5BZ | 4.4 | 4.9 | 4.7 | 4.7 | 3.3 | 4.8 | 4.1 |
| Virtue | 4.8 | 4.7 | 4.7 | 3.3 | 3.0 | 5.3 | 4.1 |
| 10752 | 3.7 | 3.7 | 3.7 | 5.0 | 3.8 | 4.2 | 4.0 |
| 10758 | 4.2 | 3.9 | 4.1 | 3.0 | 4.0 | 4.1 | 4.0 |
| 10769 | 4.4 | 4.0 | 4.2 | 4.7 | 3.0 | 5.0 | 4.0 |
| Barlexas | 4.8 | 4.4 | 4.6 | 4.0 | 5.0 | 3.1 | 4.0 |
| Dominion | 3.9 | 4.3 | 4.1 | 3.7 | 3.4 | 4.5 | 4.0 |
| Falcon II | 4.0 | 3.5 | 3.8 | 4.3 | 3.6 | 4.5 | 4.0 |
| PST-R5EL | 4.4 | 4.0 | 4.2 | 5.3 | 3.1 | 4.9 | 4.0 |
| Southern Choice | 4.4 | 3.7 | 4.1 | 5.0 | 2.9 | 5.2 | 4.0 |
| PST-5PL | 3.9 | 4.6 | 4.3 | 4.0 | 3.3 | 4.4 | 3.9 |
| Dynamic | 5.0 | 5.1 | 5.1 | 2.3 | 3.4 | 4.3 | 3.9 |
| MRF 29 | 3.1 | 3.3 | 3.2 | 3.0 | 2.9 | 4.8 | 3.9 |
| PST-53T | 4.3 | 5.5 | 4.9 | 4.3 | 3.7 | 4.1 | 3.9 |
| TF66 | 4.6 | 4.4 | 4.5 | 4.0 | 3.8 | 4.1 | 3.9 |
| 10756 | 3.3 | 3.0 | 3.1 | 4.0 | 2.9 | 4.8 | 3.8 |
| 10760 | 3.9 | 4.5 | 4.2 | 1.7 | 3.0 | 4.6 | 3.8 |
| PST-5KB | 4.5 | 4.1 | 4.3 | 5.0 | 3.4 | 4.3 | 3.8 |
| Barrington | 4.7 | 4.1 | 4.4 | 4.0 | 2.7 | 4.9 | 3.8 |
| Grande | 3.8 | 3.7 | 3.8 | 2.3 | 3.1 | 4.5 | 3.8 |
| Laramie | 3.9 | 3.5 | 3.7 | 4.3 | 3.1 | 4.5 | 3.8 |
| Millennium | 4.6 | 3.9 | 4.3 | 5.7 | 4.1 | 3.6 | 3.8 |
| Sunpro | 4.5 | 4.5 | 4.5 | 3.0 | 3.3 | 4.3 | 3.8 |
| T991 | 4.1 | 3.9 | 4.0 | 3.3 | 3.3 | 4.3 | 3.8 |
| Watchdog | 2.8 | 4.0 | 3.4 | 4.3 | 2.3 | 5.2 | 3.8 |
| PST-5DH | 4.2 | 3.8 | 4.0 | 5.0 | 3.2 | 4.3 | 3.7 |
| Tahoe | 4.0 | 3.9 | 4.0 | 4.3 | 1.9 | 5.6 | 3.7 |
| Coronado Gold | 5.1 | 4.9 | 5.0 | 5.0 | 3.6 | 3.8 | 3.7 |
| Stetson | 3.8 | 3.9 | 3.8 | 3.0 | 2.3 | 5.0 | 3.7 |
| Tomahawk GT | 4.5 | 3.1 | 3.8 | 4.0 | 2.2 | 5.1 | 3.7 |
| Tracer | 3.9 | 4.3 | 4.1 | 4.0 | 3.1 | 4.3 | 3.7 |
| 10750 | 4.2 | 4.3 | 4.2 | 3.0 | 3.1 | 4.2 | 3.6 |
| Bravo | 3.9 | 3.9 | 3.9 | 3.7 | 3.9 | 3.3 | 3.6 |
| Coronado | 4.0 | 3.3 | 3.6 | 2.7 | 2.3 | 4.9 | 3.6 |
| Eldorado | 3.2 | 2.9 | 3.0 | 5.3 | 2.6 | 4.7 | 3.6 |
| PST-5PHR | 4.3 | 3.9 | 4.1 | 4.3 | 2.7 | 4.5 | 3.6 |
| MRF 25 | 4.4 | 4.3 | 4.4 | 3.0 | 3.2 | 3.8 | 3.5 |
| Crewcut | 4.2 | 3.6 | 3.9 | 3.3 | 3.2 | 3.7 | 3.4 |
| PST-5LMD | 3.3 | 2.6 | 2.9 | 3.3 | 2.0 | 4.6 | 3.3 |
| Barrera | 3.8 | 3.5 | 3.7 | 5.0 | 2.8 | 3.8 | 3.3 |
| Kentucky 31 | 2.3 | 2.1 | 2.2 | 3.0 | 3.6 | 3.1 | 3.3 |
| BAR Fa 1CR7 | 4.2 | 3.7 | 4.0 | 2.7 | 2.6 | 3.8 | 3.2 |
| MRF 22 | 4.4 | 3.9 | 4.1 | 5.3 | 2.6 | 3.8 | 3.2 |
| Lancer E | 4.3 | 2.8 | 3.5 | 3.0 | 2.0 | 3.9 | 3.0 |

TABLE 12-continued

Mean turf quality, Pythium blight, and brown patch ratings for tall fescue turf trial seeded fall of 2001 near Rolesville, NC

| Variety | Turf Quality 2002 | 2003 | Mean | Pythium 21 Aug. 2003 | Brown Patch 2002 | 2003 | Mean |
|---|---|---|---|---|---|---|---|
| Bonsai | 3.6 | 1.1 | 2.3 | 2.7 | 2.3 | 2.4 | 2.4 |
| LSD (0.05) | 1.1 | 1.4 | 1.2 | 2.4 | 1.7 | 2.0 | 1.3 |

*To determine statistical differences among entries, subtract one entry's mean from another entry's mean. Statistical differences occur when this value is equal to or larger than the corresponding L.S.D. value.

TABLE 13

2003 mean cool-season Rhizoctonia and turf quality ratings for tall fescue turf trial seeded fall of 2002 near Hubbard, OR

| Variety | Cool-Season Rhizoctonia | Turf Quality Jan-Mar | Apr-Jun | Jul-Sep | Oct-Dec | Mean |
|---|---|---|---|---|---|---|
| Dynamic | 7.7 | 6.9 | 7.7 | 6.8 | 7.3 | 7.2 |
| PST-5KB | 6.7 | 6.8 | 8.2 | 7.2 | 6.7 | 7.2 |
| PST-DDL | 8.0 | 7.3 | 8.0 | 6.7 | 6.7 | 7.2 |
| PST-53T | 8.0 | 6.9 | 8.0 | 6.5 | 7.0 | 7.1 |
| Finesse II | 8.0 | 7.2 | 8.0 | 6.3 | 6.3 | 7.0 |
| Matador GT | 7.7 | 7.4 | 8.2 | 6.3 | 6.2 | 7.0 |
| PST-5SHZ | 8.0 | 7.6 | 8.0 | 6.2 | 6.2 | 7.0 |
| Apache III | 8.0 | 6.8 | 7.3 | 6.7 | 6.7 | 6.9 |
| PST-5JM | 8.3 | 7.1 | 7.2 | 6.8 | 6.7 | 6.9 |
| Silverstar | 8.0 | 7.2 | 7.5 | 6.7 | 6.0 | 6.8 |
| 2nd Millennium | 8.0 | 6.8 | 6.8 | 6.7 | 6.5 | 6.7 |
| PST-5FZ | 7.0 | 6.3 | 7.5 | 6.7 | 6.3 | 6.7 |
| PST-5FZD | 7.3 | 6.4 | 7.7 | 6.7 | 6.2 | 6.7 |
| PST-5KI | 7.0 | 6.4 | 8.0 | 6.3 | 6.2 | 6.7 |
| PST-5UP | 7.0 | 6.2 | 7.7 | 6.3 | 6.7 | 6.7 |
| Fidelity | 7.3 | 6.9 | 7.2 | 6.3 | 6.2 | 6.6 |
| PST-5BZ | 7.0 | 6.3 | 7.0 | 6.3 | 6.8 | 6.6 |
| PST-5L1 | 7.3 | 6.1 | 8.5 | 6.2 | 5.7 | 6.6 |
| PST-L1F | 7.3 | 6.8 | 7.3 | 6.3 | 5.8 | 6.6 |
| PST-5BAB | 8.7 | 7.0 | 7.2 | 5.7 | 6.0 | 6.5 |
| PST-5L0 | 6.3 | 6.3 | 7.2 | 6.2 | 6.5 | 6.5 |
| PST-5V2 | 7.3 | 6.6 | 6.8 | 6.5 | 6.2 | 6.5 |
| Silverado II | 7.3 | 6.6 | 6.7 | 6.3 | 6.3 | 6.5 |
| Coronado | 8.3 | 7.2 | 6.7 | 6.0 | 5.7 | 6.4 |
| Matador | 7.0 | 6.2 | 7.7 | 6.2 | 5.7 | 6.4 |
| PST-5S12 | 6.7 | 6.1 | 7.2 | 6.0 | 6.5 | 6.4 |
| PST-5BUL | 7.7 | 6.0 | 7.0 | 6.2 | 6.2 | 6.3 |
| PST-5R4T | 7.3 | 6.0 | 7.2 | 6.0 | 6.2 | 6.3 |
| PST-5V1 | 7.3 | 6.3 | 6.3 | 6.3 | 6.3 | 6.3 |
| Pure Gold | 7.3 | 5.7 | 7.5 | 5.8 | 6.2 | 6.3 |
| PST-5NAS | 6.7 | 5.6 | 6.8 | 6.3 | 6.0 | 6.2 |
| PST-5PAL | 7.7 | 6.1 | 6.3 | 6.7 | 5.7 | 6.2 |
| PST-5S1 | 7.0 | 5.7 | 6.3 | 6.5 | 6.3 | 6.2 |
| Tomahawk GT | 6.7 | 6.3 | 7.2 | 5.5 | 5.7 | 6.2 |
| Dominion | 7.0 | 6.2 | 6.8 | 5.7 | 5.8 | 6.1 |
| Mowless | 7.3 | 5.8 | 6.2 | 5.7 | 6.7 | 6.1 |
| Tar Heel II | 6.3 | 5.4 | 6.3 | 6.3 | 6.0 | 6.0 |
| Wolfpack | 7.7 | 5.7 | 6.3 | 5.5 | 6.5 | 6.0 |
| Jaguar 3 | 7.0 | 5.9 | 6.2 | 5.7 | 5.8 | 5.9 |
| PST-5BET | 7.3 | 5.8 | 6.5 | 5.5 | 5.7 | 5.9 |
| Triathalawn | 8.0 | 6.6 | 6.7 | 5.2 | 5.2 | 5.9 |
| Bonanza II | 6.7 | 5.8 | 6.3 | 5.5 | 5.5 | 5.8 |
| Southern Gold | 7.3 | 5.6 | 5.8 | 5.5 | 6.2 | 5.8 |
| Summer Lawn | 7.7 | 5.3 | 6.5 | 5.8 | 5.5 | 5.8 |
| Tar Heel | 6.7 | 5.3 | 6.0 | 5.7 | 6.0 | 5.8 |
| Bandana | 7.3 | 5.4 | 5.7 | 5.5 | 6.2 | 5.7 |
| Confederate Plus | 7.3 | 5.3 | 5.0 | 6.0 | 6.3 | 5.7 |
| Coronado Gold | 6.7 | 5.3 | 5.5 | 6.2 | 5.8 | 5.7 |
| Olympic Gold | 6.7 | 5.8 | 5.7 | 5.5 | 6.0 | 5.7 |
| Southern Gold Plus | 6.3 | 4.9 | 6.2 | 5.5 | 6.2 | 5.7 |
| Tomahawk | 6.3 | 5.9 | 5.7 | 5.5 | 5.7 | 5.7 |
| Adventure II | 7.3 | 5.3 | 5.3 | 5.3 | 6.3 | 5.6 |
| Apache II | 6.3 | 5.7 | 6.2 | 5.0 | 5.7 | 5.6 |
| Bonsai | 6.7 | 5.7 | 5.8 | 5.0 | 5.8 | 5.6 |
| Endure | 6.3 | 5.2 | 5.8 | 5.3 | 6.2 | 5.6 |
| Murietta | 7.7 | 5.2 | 5.3 | 5.7 | 6.2 | 5.6 |
| Shortstop II | 7.0 | 5.3 | 5.7 | 5.2 | 5.3 | 5.4 |
| Crossfire II | 6.7 | 5.2 | 5.2 | 5.3 | 5.5 | 5.3 |
| Confederate | 7.0 | 5.2 | 5.2 | 5.5 | 5.5 | 5.3 |
| Endeavor | 6.7 | 5.1 | 5.2 | 5.2 | 5.7 | 5.3 |
| Safari | 7.3 | 5.3 | 5.0 | 5.2 | 5.5 | 5.3 |
| Eldorado | 8.0 | 5.6 | 5.2 | 4.7 | 5.2 | 5.1 |
| Grande | 6.7 | 5.2 | 4.8 | 5.0 | 5.2 | 5.1 |
| Mustang II | 7.7 | 5.7 | 4.7 | 4.8 | 5.2 | 5.1 |
| Stetson | 7.7 | 5.0 | 4.8 | 5.2 | 5.5 | 5.1 |
| Avanti | 7.0 | 5.3 | 4.3 | 5.3 | 5.2 | 5.0 |
| PST-5NM | 7.3 | 4.8 | 4.3 | 4.7 | 5.2 | 4.7 |
| Kentucky 31 | 7.7 | 2.9 | 2.8 | 3.7 | 4.3 | 3.4 |
| LSD (0.05) | 1.4 | 1.0 | 1.0 | 1.0 | 1.0 | 0.7 |

*To determine statistical differences among entries, subtract one entry's mean from another entry's mean. Statistical differences occur when this value is equal to or larger than the corresponding L.S.D. value.

TABLE 14

2003 mean turf quality, Pythium blight and brown patch ratings for tall fescue turf trial seeded fall of 2002 near Rolesville, NC

| Entry | Turf Quality Jan-Mar | Apr-Jun | Jul-Sep | Oct-Dec | Mean | Pythium 21 Aug | Brown Patch |
|---|---|---|---|---|---|---|---|
| Tar Heel II | 5.2 | 5.2 | 4.8 | 5.7 | 5.2 | 3.7 | 6.9 |
| Tar Heel | 5.0 | 5.0 | 3.8 | 3.1 | 4.2 | 4.7 | 6.7 |
| Southern Gold | 5.7 | 5.7 | 3.3 | 3.7 | 4.6 | 3.3 | 6.6 |
| PST-5L0 | 5.0 | 4.8 | 4.5 | 5.4 | 4.9 | 4.7 | 6.3 |
| PST-5V1 | 5.3 | 5.3 | 5.2 | 5.2 | 5.3 | 3.0 | 6.3 |
| Endeavor | 6.2 | 5.6 | 4.3 | 4.0 | 5.0 | 2.7 | 6.0 |
| Olympic Gold | 5.7 | 5.6 | 4.2 | 4.1 | 4.9 | 4.0 | 6.0 |
| PST-5FZ | 5.2 | 5.8 | 4.3 | 3.7 | 4.7 | 2.7 | 5.9 |
| Wolfpack | 5.3 | 4.7 | 4.0 | 4.4 | 4.6 | 5.7 | 5.9 |
| PST-5BAB | 4.8 | 4.6 | 4.0 | 5.1 | 4.6 | 3.3 | 5.8 |
| PST-5KI | 5.5 | 5.2 | 4.5 | 5.0 | 5.0 | 4.0 | 5.8 |
| Rebel Sentry | 4.7 | 4.3 | 3.7 | 3.8 | 4.1 | 2.7 | 5.8 |
| Safari | 5.7 | 4.3 | 3.0 | 3.1 | 4.0 | 4.0 | 5.8 |
| PST-53T | 5.3 | 4.8 | 4.3 | 4.6 | 4.7 | 4.7 | 5.7 |
| Syn R5IL | 5.0 | 4.4 | 4.5 | 5.6 | 4.9 | 4.3 | 5.7 |
| Silverado II | 4.5 | 4.7 | 4.3 | 4.9 | 4.6 | 3.7 | 5.6 |
| Summer Lawn | 5.7 | 5.2 | 3.7 | 3.4 | 4.5 | 3.7 | 5.6 |
| Syn 5R4T | 4.3 | 4.5 | 4.0 | 3.7 | 4.1 | 4.0 | 5.6 |
| 2nd Millennium | 5.2 | 4.8 | 4.3 | 3.9 | 4.5 | 3.7 | 5.5 |
| PST-5S12 | 5.5 | 5.4 | 3.8 | 4.2 | 4.7 | 2.7 | 5.5 |
| PST-L1F | 5.7 | 5.8 | 5.2 | 4.2 | 5.2 | 3.3 | 5.5 |
| Dynamic | 5.5 | 5.3 | 3.8 | 4.1 | 4.7 | 2.0 | 5.4 |
| Matador GT | 6.0 | 6.3 | 5.0 | 4.7 | 5.5 | 4.7 | 5.4 |
| Apache III | 5.7 | 5.4 | 4.2 | 4.1 | 4.8 | 3.0 | 5.3 |
| Dynasty | 4.7 | 4.6 | 3.5 | 4.0 | 4.2 | 3.3 | 5.3 |
| Grande | 5.5 | 4.3 | 3.0 | 3.2 | 4.0 | 3.7 | 5.3 |
| Shortstop | 3.3 | 3.3 | 2.8 | 2.4 | 3.0 | 2.0 | 5.3 |
| Bandana | 4.5 | 4.0 | 3.2 | 2.9 | 3.6 | 4.7 | 5.2 |
| Syn R5L11 | 5.5 | 5.5 | 5.2 | 5.7 | 5.5 | 4.0 | 5.2 |
| PST-5FZD | 5.5 | 5.2 | 3.3 | 2.9 | 4.2 | 3.0 | 5.1 |
| Adventure II | 5.0 | 4.8 | 3.2 | 2.6 | 3.9 | 2.0 | 5.0 |
| Durana | 5.0 | 4.7 | 3.7 | 3.9 | 4.3 | 2.7 | 5.0 |

TABLE 14-continued 2003 mean turf quality, Pythium blight and brown patch ratings for tall fescue turf trial seeded fall of 2002 near Rolesville, NC

| Entry | Turf Quality | | | | | Pythium 21 Aug | Brown Patch |
|---|---|---|---|---|---|---|---|
| | Jan-Mar | Apr-Jun | Jul-Sep | Oct-Dec | Mean | | |
| PST-5UP | 5.3 | 4.9 | 3.5 | 2.0 | 3.9 | 2.0 | 5.0 |
| Silverstar | 5.8 | 5.5 | 4.3 | 4.0 | 4.9 | 4.0 | 5.0 |
| Syn 5L1 | 5.5 | 5.6 | 4.8 | 5.9 | 5.5 | 4.0 | 5.0 |
| Dominion | 4.2 | 4.0 | 3.7 | 4.0 | 4.0 | 3.3 | 4.9 |
| PST-5JM | 5.5 | 4.4 | 3.5 | 4.7 | 4.5 | 4.0 | 4.9 |
| Syn 5BET | 4.5 | 4.4 | 3.5 | 4.4 | 4.2 | 2.7 | 4.9 |
| Finesse II | 5.3 | 5.0 | 3.3 | 3.3 | 4.3 | 2.7 | 4.8 |
| Mowless | 4.5 | 4.8 | 3.7 | 3.7 | 4.2 | 4.3 | 4.8 |
| Murietta | 5.5 | 4.7 | 5.2 | 6.2 | 5.4 | 5.7 | 4.8 |
| PST-5BZ | 5.2 | 5.7 | 4.5 | 5.0 | 5.1 | 4.3 | 4.8 |
| Pure Gold | 3.0 | 2.8 | 3.3 | 4.1 | 3.3 | 5.3 | 4.8 |
| OnCue | 5.3 | 5.2 | 3.8 | 3.7 | 4.5 | 1.7 | 4.7 |
| Syn 5NM | 5.2 | 4.3 | 4.3 | 3.4 | 4.3 | 4.0 | 4.7 |
| Avanti | 4.5 | 4.2 | 3.0 | 1.8 | 3.4 | 4.3 | 4.6 |
| Focus | 4.5 | 4.2 | 3.3 | 3.1 | 3.8 | 4.0 | 4.6 |
| Plantation | 5.7 | 4.9 | 3.3 | 2.9 | 4.2 | 3.7 | 4.6 |
| Fidelity | 5.5 | 5.6 | 5.7 | 6.2 | 5.7 | 5.3 | 4.6 |
| Coronado Gold | 6.0 | 5.8 | 4.2 | 4.3 | 5.1 | 3.7 | 4.5 |
| Mustang II | 4.7 | 4.7 | 3.3 | 2.3 | 3.8 | 2.3 | 4.5 |
| SunPro | 4.8 | 5.1 | 3.2 | 3.9 | 4.2 | 2.0 | 4.5 |
| South Paw | 4.5 | 4.3 | 3.2 | 2.7 | 3.7 | 3.3 | 4.4 |
| PST-5S1 | 5.5 | 4.9 | 3.5 | 4.1 | 4.5 | 3.7 | 4.4 |
| Syn R5L1F | 6.0 | 5.8 | 4.2 | 3.9 | 5.0 | 3.0 | 4.4 |
| Apache II | 5.0 | 4.5 | 3.3 | 4.0 | 4.2 | 2.7 | 4.3 |
| Endure | 4.8 | 5.1 | 4.0 | 3.6 | 4.4 | 3.3 | 4.3 |
| Syn 5BUL | 5.5 | 5.1 | 3.7 | 4.6 | 4.7 | 4.7 | 4.3 |
| Syn 5PAL | 5.5 | 5.7 | 5.2 | 5.8 | 5.5 | 4.7 | 4.3 |
| PST-DDL | 4.8 | 4.1 | 3.8 | 4.3 | 4.3 | 3.3 | 4.2 |
| Jaguar 3 | 4.2 | 3.8 | 3.8 | 3.3 | 3.8 | 4.3 | 4.1 |
| Triathalawn | 6.0 | 5.5 | 3.7 | 4.2 | 4.8 | 4.3 | 4.1 |
| Matador | 6.0 | 5.8 | 3.5 | 3.3 | 4.6 | 5.0 | 4.0 |
| PST-5KB | 4.7 | 4.3 | 3.3 | 3.8 | 4.0 | 2.7 | 4.0 |
| Syn 5V2 | 5.5 | 5.4 | 4.3 | 4.3 | 4.9 | 4.0 | 4.0 |
| Transition Blend | 5.3 | 5.0 | 4.0 | 4.7 | 4.8 | 4.0 | 4.0 |
| Crossfire II | 2.8 | 2.6 | 2.2 | 3.0 | 2. | 1.7 | 3.9 |
| Millennium | 5.3 | 3.9 | 3.3 | 4.8 | 4.3 | 4.0 | 3.8 |
| PST-5NAS | 4.7 | 4.8 | 3.8 | 3.7 | 4.2 | 5.0 | 3.8 |
| Eldorado | 5.2 | 3.6 | 2.5 | 2.7 | 3.5 | 4.0 | 3.7 |
| Tomahawk | 5.2 | 5.0 | 4.2 | 4.7 | 4.8 | 5.0 | 3.7 |
| Tomahawk GT | 5.5 | 5.5 | 3.3 | 2.9 | 4.3 | 3.7 | 3.6 |
| MRF 22 | 5.7 | 4.8 | 2.8 | 2.8 | 4.0 | 3.3 | 3.5 |
| Duster | 4.0 | 3.8 | 3.2 | 3.2 | 3.6 | 3.0 | 3.4 |
| Bonsai | 5.0 | 4.8 | 2.8 | 3.2 | 4.0 | 3.7 | 3.3 |
| Coronado | 6.0 | 5.8 | 3.8 | 3.9 | 4.9 | 3.7 | 3.3 |
| Kentucky 31 | 2.8 | 2.2 | 2.0 | 2.0 | 2.3 | 2.7 | 3.3 |
| Daytona | 4.7 | 4.2 | 2.5 | 3.4 | 3.7 | 2.0 | 3.3 |
| Rebel Exeda | 5.5 | 4.9 | 4.0 | 4.0 | 4.6 | 2.7 | 3.0 |
| Rebel III | 4.8 | 5.2 | 3.2 | 3.6 | 4.2 | 2.7 | 2.9 |
| Southeast | 2.2 | 2.0 | 2.2 | 2.0 | 2.1 | 1.3 | 2.7 |
| Rebel 2000 | 3.0 | 2.5 | 2.2 | 2.4 | 2.5 | 3.3 | 2.5 |
| The Rebels | 3.8 | 4.3 | 2.7 | 3.2 | 3.5 | 2.3 | 2.3 |
| Water Saver | 4.2 | 3.5 | 2.5 | 3.8 | 3.5 | 1.7 | 2.3 |
| LSD (0.05) | 1.1 | 1.3 | 1.2 | 1.8 | 0.9 | 2.6 | 1.7 |

*To determine statistical differences among entries, subtract one entry's mean from another entry's mean. Statistical differences occur when this value is equal to or larger than the corresponding L.S.D. value.

EXAMPLE 6

Glyphosate Tolerance Characteristics

The following tables show examples of field trials in which the glyphosate resistance characteristics of the Matador GT variety were examined and compared to other tall fescue grass varieties, some of which are also glyphosate tolerant (such as the Tomahawk GT and Pure Gold GT varieties). Grasses were seeded in the fall of 2002 or 2003 near Hubbard, Oreg. and rated 2-14 weeks after treatment (WAT).

Table 15 shows comparisons of the turf quality of the Matador GT variety with other tall fescue varieties in the presence of 4 oz/acre, 8 oz/acre, or 16 oz/acre glyphosate herbicide (Credit®, Nufarm, Inc., Australia). The data is presented as the mean percent herbicide damage 4 weeks after treatment. This turf trial was seeded on Sep. 4, 2002 and sprayed with glyphosate herbicide on Apr. 16, 2003.

TABLE 15

Tall fescues in the presence of 4, 8 or 16 ounces per acre Credit ®.

| Entry | 4 oz | 8 oz | 16 oz |
|---|---|---|---|
| Tomahawk GT | 0.0 | 2.5 | 45.0 |
| Pure Gold | 0.0 | 5.0 | 45.0 |
| Matador GT | 0.0 | 2.5 | 62.5 |
| Tomahawk | 5.0 | 27.5 | 85.0 |
| Annual Ryegrass | 0.0 | 25.0 | 95.0 |
| LSD (0.05)* | 7.4 | 33.7 | 56.5 |

*To determine statistical differences among entries, subtract one entry's mean from another entry's mean. Statistical differences occur when this value is equal to or larger than the corresponding L.S.D. value.

Table 16 shows comparisons of the turf quality of the Matador GT variety with other tall fescue varieties in the presence of 4 oz/acre glyphosate herbicide (Roundup Ultra Max®, Monsanto, St. Louis, Mo.). The data is presented as the mean percent herbicide survival 4 weeks or 6 months after treatment. This turf trial was seeded on Sep. 4, 2002 and sprayed with glyphosate herbicide on Nov. 5, 2002.

TABLE 16

Tall fescues in the presence of 4 ounces per acre Roundup Ultra Max ®.

| Entry | 8 weeks after Treatment | 6 months after treatment |
|---|---|---|
| Tomahawk GT | 50.0* | 100.0 |
| Matador GT | 50.0* | 90.0 |
| Pure Gold | 40.0* | 95.0 |
| Tomahawk | 75.0 | 75.0 |
| Annual Ryegrass | 60.0 | 30.0 |
| LSD (0.05)# | 24.8 | 34.0 |

*= Significant difference at 0.05 level from non-tolerant check and annual ryegrass weed.
To determine statistical differences among entries, subtract one entry's mean from another entry's mean. Statistical differences occur when this value is equal to or larger than the corresponding L.S.D. value.

Table 17 shows comparisons of the turf quality of the Matador GT variety with other tall fescue varieties in the presence of 4 or 8 oz/acre glyphosate herbicide (Razor Pro®, Nurfarm Turf and Specialty, Burr Ridge, Ill.). The data is presented as the mean percent herbicide survival 8 weeks after treatment. This turf trial was seeded on Sep. 4, 2002 and sprayed with glyphosate herbicide on Mar. 19, 2003.

TABLE 17

Tall fescues in the presence of 4 or 8 ounces per acre Razor Pro ®.

| Entry | 4 oz | 8 oz |
|---|---|---|
| Tomahawk | 100 | 100 |
| Matador GT | 100 | 100 |
| Pure Gold | 100 | 100 |
| Tomahawk GT | 100 | 100 |

TABLE 17-continued

Tall fescues in the presence of 4 or 8 ounces per acre Razor Pro ®.

| Entry | 4 oz | 8 oz |
|---|---|---|
| Annual Ryegrass | 100 | 75 |
| LSD (0.05)* | NS | 37.1 |

*To determine statistical differences among entries, subtract one entry's mean from another entry's mean. Statistical differences occur when this value is equal to or larger than the corresponding L.S.D. value.

Table 18 shows comparisons of the turf quality of the Matador GT variety with other tall fescue varieties in the presence of 8 oz/acre glyphosate herbicide (Razor®, Nurfarm Turf and Specialty). The data is presented as the mean percent herbicide damage 2, 3 or 7 weeks after treatment. This turf trial was seeded in the fall of 2003 and sprayed with glyphosate herbicide on Nov. 7, 2003 or Mar. 22, 2004.

TABLE 18

Tall fescues in the presence of 8 ounces per acre Razor ®#

| | | 07 Nov. 2003 | | 22 Mar. 2004 |
|---|---|---|---|---|
| Entry | Species | 2 WAT* | 7 WAT | 3 WAT |
| Seabreeze GT | Slender creeping fescue | 27.5 | 33.5 | 8.5 |
| Pure Gold | Tall fescue | 62.5 | 41.0 | 9.0 |
| Quicksilver | Perennial Ryegrass | 28.5 | 24.5 | 9.0 |
| Matador GT | Tall fescue | 45.0 | 28.5 | 13.5 |
| Tomahawk GT | Tall fescue | 50.0 | 42.5 | 20.0 |
| Florentine GT | Strong creeping fescue | 47.5 | 45.0 | 38.5 |
| LSD (0.05) | | 26.3 | 32.2 | 19.4 |

*WAT = weeks after treatment
All varieties had 100% recovery by 14 weeks after treatment.

The data above demonstrate that Matador GT plants are tolerant to glyphosate herbicide applied at levels and/or frequency sufficient to remove weed species, for example from sod, lawns, pasture, golf courses, athletic fields, etc. As used herein the phrase "a glyphosate tolerant grass plant" is a grass plant that will survive application of agricultural formulations of glyphosate herbicide (containing 41% w/v glyphosate) at levels equivalent to up to ½ pint (8 oz.) per acre, corresponding to at least about 0.056 g per square meter of active ingredient glyphosate. This level of glyphosate is sufficient to kill some common grass weeds. Matador GT may tolerate additional applications of ¼ or ½ pint per acre of glyphosate herbicide the following spring or fall after seeding, where necessary to remove weeds that are difficult to control. However, when re-applying glyphosate herbicide, the sensitivity of the Matador GT variety to ambient temperature, time of year, and age of the grass should be considered.

EXAMPLE 7

Brown Patch Resistance

To determine brown patch resistance of Matador GT, the following methods were used. A tall fescue turf trial was seeded in the fall of 2001 at six locations (Fayetteville, Ark.; Carbondale, Ill.; West Lafayette, Ind.; Stillwater, Okla.; Blacksburg, Va.; and Madison, Wis.). The mean brown patch rating for the Matador GT variety in 2002 was 5.9 (9=no disease). As shown in Table 19 (as well as Tables 12 and 14), Matador GT has moderate brown patch resistance.

TABLE 19

2002 mean brown patch ratings for national tall fescue turf trials.

| Variety | AR1 | IL2 | IN1 | OK1 | VA1 | WI1 | Mean |
|---|---|---|---|---|---|---|---|
| Kentucky 31 | 8.0 | 5.7 | 8.7 | 3.0 | 8.7 | 8.0 | 7.0 |
| Tar Heel | 7.3 | 4.3 | 8.0 | 3.3 | 8.0 | 8.3 | 6.6 |
| Matador | 5.7 | 4.7 | 8.0 | 3.7 | 7.3 | 7.7 | 6.2 |
| Matador GT | 5.7 | 3.7 | 7.3 | 3.3 | 7.0 | 8.3 | 5.9 |
| DP 50-9082 | 4.3 | 2.7 | 6.7 | 4.7 | 4.7 | 7.7 | 5.1 |
| LSD (0.05)* | 3.3 | 3.3 | 1.5 | 1.6 | 2.4 | 0.9 | 1.0 |

*To determine statistical differences among entries, subtract one entry's mean from another entry's mean. Statistical differences occur when this value is equal to or larger than the corresponding L.S.D. value.

These results show that the Matador GT variety has both tolerance to glyphosate herbicides and moderate brown patch resistance.

EXAMPLE 8

Rust resistance

To determine rust resistance of Matador GT, the following methods were used. A tall fescue turf trial was seeded in the fall of 2001 near Hubbard, Oreg. The mean stem rust rating for the Matador GT variety in 2002 was 7.0 (9=no disease). As shown in Table 20, Matador GT has good stem rust resistance.

TABLE 20

2002 mean stem rust ratings for entries in a tall fescue seed yield trial

| Variety | Mean |
|---|---|
| Matador | 7.0 |
| Matador GT | 7.0 |
| Kentucky 31 | 6.0 |
| Tar Heel | 4.0 |
| Silverado | 3.0 |
| Eldorado | 2.0 |
| LSD (0.05)* | 2.2 |

*To determine statistical differences among entries, subtract one entry's mean from another entry's mean. Statistical differences occur when this value is equal to or larger than the corresponding L.S.D. value.

EXAMPLE 9

Salt Tolerance

To determine the salt tolerance of Matador GT, the following methods were used. A tall fescue turf trial was seeded in the fall of 2001 near Hubbard, Oreg. The tall fescue entries were then placed in a greenhouse salt bath at 25,000 ppm NaCl on 11 Jul. 2002, and the mean salt damage rating determined on 29 Jul. 2002, 16 Aug. 2002 and 11 Sep. 2002. In addition, a determination of the number of plants alive on 11 Sep. 2002 and 24 Oct. 2002 was determined. The mean salt damage rating for the Matador GT variety in 2002 was between 2.3 and 1.7 (5=no damage). As shown in Table 21, Matador GT has moderate salt tolerance.

TABLE 21

2002 mean salt damage ratings for tall fescue entries

| Variety | Salt Damage | | | # Alive | |
|---|---|---|---|---|---|
| | 29 Jul. | 16 Aug. | 11 Sep. | 11 Sep. | 24 Oct. |
| Kentucky 31 | 2.7 | 1.7 | 1.7 | 35* | 26 |
| Matador GT | 2.3 | 2.0 | 1.7 | 30 | 21 |
| Silverado | 3.0 | 1.7 | 1.7 | 27 | 19 |
| Matador | 2.7 | 1.3 | 1.0 | 19 | 14 |
| LSD (0.05) | 1.0 | 1.0 | 0.8 | 11 | 12 |

*original n = 42

EXAMPLE 10

Production of Glyphosate-Tolerant Grasses

Matador GT can be grown under normal conditions for growing turf grasses, and bulk seed for large-scale planting can be obtained by methods known in certified seed production. For example, bulk seed can be produced by planting Matador GT variety seeds obtained from either ATCC(PTA-5790) or Pure Seed Testing, Inc., allowing the mature plants to produce seed by cross-pollination with each other and then collecting the seed. Standard precautions can be taken to prevent cross-pollination from other grasses, such as growing the variety in an isolated plot of sterilized soil, and removing adjacent vegetation. The Matador GT variety seeds deposited with ATCC are breeder seeds; propagation of plants from these seeds can be performed under the conditions specified in the 1998 Oregon Certified Seed Handbook, published by Oregon State University Extension Service, Corvallis, Oreg. 97331.

The Matador GT variety can also be asexually reproduced via vegetative propagules, such as sprigs, plugs, and sod.

To confirm maintenance of the glyphosate-tolerance characteristic, a glyphosate herbicide (such as one containing 41% w/v active ingredient glyphosate) can be applied to the plants at the equivalent of at least ¼ pint per acre, for example at least ½ pint per acre.

EXAMPLE 11

Exemplary Uses of the Glyphosate Tolerant Grass Matador GT

The tall fescue variety Matador GT can be used in the same way as other tall fescue varieties. However, the resistance to glyphosate herbicides affords the Matador GT variety particular advantages over other varieties. For example, with current commercially available varieties of fescue grasses, the preparation of a lawn that is to be made by seeding requires extensive preparation of the soil to remove weeds that may be present, often including soil fumigation. With Matador GT, such preparation can be avoided since some weeds that begin to grow in the new lawn are readily removed by application of a glyphosate herbicide. With Matador GT, glyphosate herbicides can also be used to remove many of the most troublesome lawn weeds such as crabgrass (*Digitaria sanguinalis*), annual bluegrass (*Poa annua*), rattail fescue (*Vulpia myuros*) and annual ryegrass (*Lolium multiforum*). Thus, the Matador GT variety is especially marketable and therefore useful.

EXAMPLE 12

Introducing Traits of the Matador GT Variety Into Other Grass Varieties

The morphological and physiological characteristics of the Matador GT variety of tall fescue, including the glyphosate tolerance trait, can be introduced into other grass varieties by conventional breeding techniques. For example, the Matador GT variety can be grown in pollination proximity to another variety of tall fescue grass, allowing cross-pollination to occur between the Matador GT variety and the other variety, and then harvesting the hybrid seeds. Plants grown from these hybrid seeds can then be tested for the maintenance of the molecular characteristics described above for the Matador GT variety, or the plants can simply be observed to see if they display the same growth characteristics described in one or more of the above tables.

For example, plants grown from these hybrid seeds can be tested for glyphosate tolerance by application of glyphosate herbicide at various levels. In this way, the glyphosate tolerance characteristic may be combined with other desirable plant characteristics; Thus, the provision of Matador GT enables the production of progeny plants of Matador GT having the glyphosate tolerance characteristic. "Progeny plants" of Matador GT are any plants that are the offspring of a cross between Matador GT and any other plant or plants. Progeny plants also include successive generations of the offspring, for example those selected for glyphosate tolerance using the methods described herein. First-generation progeny plants may retain the glyphosate tolerance characteristic of the Matador GT parent. However, if a first-generation progeny plant does not retain the desired level of glyphosate tolerance observed with Matador GT, subsequent generations of offspring can be recycled for glyphosate tolerance which have at least the same resistance characteristics of Matador GT described herein, such capable of tolerating application of at least about ¼ pint per acre, such as at least about ½ pint per acre, of a glyphosate herbicide (containing 41% w/v active ingredient glyphosate).

In addition, Matador GT can be used as transformation targets for the production of transgenic grasses. For example, cells derived from the Matador GT variety can be transformed with at least one transgene using methods known in the art. For example, transgenes that can be used, include, but are not limited to, transgenes that confer resistance to herbicides, insect, disease (such as viral, bacterial, fungal, nematode, infections), and drought; standability; prolificacy; salt damage resistance, and quality. Examples of such genes and methods of transforming plants are described in U.S. Pat. No. 6,025,545 to Lundquist et al., and Jain and Jain (*Indian J. Exp. Biol.* 38:6-17, 2000) herein incorporated by reference.

Having illustrated and described the principles of the disclosure in multiple embodiments and examples, it should be apparent to those skilled in the art that the disclosure can be modified in arrangement and detail without departing from such principles. The invention, therefore, encompasses all modifications coming within the spirit and scope of the following claims.

What is claimed is:

1. A tall fescue grass plant, comprising all of the morphological and physiological properties of a grass plant grown from the seed deposited under American Type Culture Collection (ATCC) No: PTA-5790.

2. A sod comprising the grass plant of claim 1.

3. A method of using the grass plant of claim 1, comprising planting the grass plant of claim 1 in a golf course fairway.

4. A method of using the grass plant of claim 1, comprising planting the grass plant of claim 1 in a golf course rough.

5. A method of using the grass plant of claim 1, comprising planting the grass plant of claim 1 in a lawn.

6. A method of using the grass plant of claim 1, comprising planting the grass plant of claim 1 in an athletic field.

7. A method of using the grass plant of claim 1, comprising planting the grass plant of claim 1 in a park.

8. A seed of the grass plant of claim 1, a representative sample of said seed having been deposited under American Type Culture Collection (ATCC) No: PTA-5790.

9. A grass seed mixture, comprising the seed of claim 8.

10. A vegetative sprig or clone of the grass plant of claim 1.

11. A method of making a transformed grass plant comprising transforming the grass plant of claim 1 with least one transgene.

12. A seed resulting from crossing the grass plant of claim 1 with a second grass plant.

13. A grass plant grown from the seed of claim 12.

14. A sod comprising the grass plant of claim 13.

15. A method of using the grass plant of claim 13 comprising planting the grass plant of claim 13 in a golf course fairway, golf course rough, lawn, athletic field, or a park.

16. The seed of claim 12, wherein the second grass plant is a tall fescue grass plant.

17. A method of producing grass seed, comprising:
growing the tall fescue grass plant of claim 1 under conditions that result in growth of the grass plants and setting of progeny seed; and
harvesting the progeny seed.

18. A grass seed produced by the method of claim 17.

19. A mixture of grass seed comprising the grass seed of claim 18.

20. A method of producing grass seed, comprising:
planting the grass seed of claim 8 under conditions that result in the germination of the seed, growth of grass plants and setting of progeny seed; and
harvesting the progeny seed.

21. A grass seed produced by the method of claim 20.

22. A mixture of grass seed comprising the grass seed of claim 21.

23. A method of producing a glyphosate-tolerant grass plant, comprising:
crossing a first grass plant with at least one other grass plant to produce progeny grass plants, wherein the first grass plant is the grass plant of claim 1; and
screening the progeny grass plants to select a progeny grass plant that is tolerant to glyphosate.

24. A glyphosate-tolerant grass plant produced by the method of claim 23.

25. A sod comprising the glyphosate-tolerant grass plant of claim 24.

26. A method of using the glyphosate-tolerant grass plant of claim 24 comprising, planting the glyphosate-tolerant grass plant of claim 24 in a golf course fairway, a golf course rough, a lawn, an athletic field, or a park.

27. A vegetative sprig or clone of the glyphosate-tolerant grass plant of claim 24.

28. A method of making a transformed grass plant comprising transforming the glyphosate-tolerant grass plant of claim 23 with at least one transgene.

29. The glyphosate-tolerant grass plant according to claim 23 wherein the grass plant is tolerant to application of up to about 0.056 g per square meter of glyphosate.

30. The glyphosate-tolerant grass plant according to claim 23 wherein the grass plant is tolerant to application of at least about 0.028 g per square meter of glyphosate.

31. A grass seed deposited as ATCC No: PTA-5790.

* * * * *

UNITED STATES PATENT AND TRADEMARK OFFICE
CERTIFICATE OF CORRECTION

PATENT NO. : 7,294,771 B1
APPLICATION NO. : 10/927420
DATED : November 13, 2007
INVENTOR(S) : Fricker et al.

It is certified that error appears in the above-identified patent and that said Letters Patent is hereby corrected as shown below:

<u>In the Specification:</u>

Column 4, line 60, "PST-5 ST" should be --PST-5ST--.

Column 4, line 67 to column 5, line 1, "Seven teen" should be --Seventeen--.

Column 10, line 25, Table 9, "PST-RSEL" should be --PST-R5EL--

Column 12, line 65, Table 12, "PST-5K1" should be --PST-5KI--.

<u>In the Claims:</u>

Column 23, line 20, claim 11, "with least one" should be --with at least one--.

Column 24, line 29, claim 28, "claim 23" should be --claim 24--.

Column 24, lines 30-31, claim 29, "claim 23" should be --claim 24--.

Column 24, lines 34-35, claim 30, "claim 23" should be --claim 24--.

Signed and Sealed this

Second Day of September, 2008

JON W. DUDAS
*Director of the United States Patent and Trademark Office*